United States Patent
Senanayake et al.

(10) Patent No.: US 10,004,455 B2
(45) Date of Patent: Jun. 26, 2018

(54) REALTIME BIOFEEDBACK MECHANISM AND DATA PRESENTATION FOR KNEE INJURY REHABILITATION MONITORING AND A SOFT REAL TIME INTELLIGENT SYSTEM THEREOF

(71) Applicant: UNIVERSITI BRUNEI DARUSSALAM, Gadong (BN)

(72) Inventors: S. M. N Arosha Senanayake, Gadong (BN); Owais Ahmed Malik, Gadong (BN)

(73) Assignee: UNIVERSITI BRUNEI DARUSSALAM, Gadong (BN)

(*) Notice: Subject to any disclaimer, the term of this patent is extended or adjusted under 35 U.S.C. 154(b) by 0 days. days.

(21) Appl. No.: 15/301,530

(22) PCT Filed: Mar. 2, 2015

(86) PCT No.: PCT/IB2015/051510
§ 371 (c)(1),
(2) Date: Oct. 3, 2016

(87) PCT Pub. No.: WO2015/150931
PCT Pub. Date: Oct. 8, 2015

(65) Prior Publication Data
US 2017/0027501 A1    Feb. 2, 2017

(30) Foreign Application Priority Data

Apr. 3, 2014 (BN) .................. BN/N/2014/0036

(51) Int. Cl.
*A61B 5/04* (2006.01)
*A61B 5/00* (2006.01)
(Continued)

(52) U.S. Cl.
CPC ............ *A61B 5/486* (2013.01); *A61B 5/0077* (2013.01); *A61B 5/04017* (2013.01);
(Continued)

(58) Field of Classification Search
CPC ... A61B 5/486; A61B 5/0077; A61B 5/04017; A61B 5/0488; A61B 5/11; A61B 5/1122;
(Continued)

(56) References Cited

U.S. PATENT DOCUMENTS 6,440,067 B1 *  8/2002  DeLuca  ............... A61B 5/0002
                                                  128/920
6,571,193 B1 *  5/2003  Unuma  ................ A43B 3/0005
                                                  340/853.2

(Continued)

FOREIGN PATENT DOCUMENTS

JP         2005-278706        10/2005
WO     WO 2013144866 A1 *  10/2013  ........... A61B 5/0488

*Primary Examiner* — Devin Henson
(74) *Attorney, Agent, or Firm* — Ming Chow; Sinorica, LLC

(57) ABSTRACT

A real time visualization method and system for evaluating and monitoring recovery progress of Anterior Cruciate Ligament reconstructed/injured subject is provided. The method includes receiving multiple super-imposed bio-signals from an electromyogram (EMG) for muscles of limbs of the patient and signals pertaining to three dimensional kinematics measurement from a motion sensor set, processing the signals to extract wavelet features and evaluating the wavelet features to determine the extent of rehabilitation and a recovery classification of the patient's limb from ACL injury. The system includes an input interface circuit, a processing module, a comparator module and an output interface circuit for providing an estimate of the extent of rehabilitation the patient's limb from ACL injury.

20 Claims, 6 Drawing Sheets

(51) Int. Cl.
*A61B 5/0488* (2006.01)
*A61B 5/11* (2006.01)
(52) U.S. Cl.
CPC .............. *A61B 5/0488* (2013.01); *A61B 5/11* (2013.01); *A61B 5/1122* (2013.01); *A61B 5/1128* (2013.01); *A61B 5/4585* (2013.01); *A61B 5/4848* (2013.01); *A61B 5/726* (2013.01); *A61B 5/7264* (2013.01); *A61B 5/1123* (2013.01); *A61B 5/1124* (2013.01); *A61B 5/4519* (2013.01); *A61B 5/4533* (2013.01); *A61B 2505/09* (2013.01)
(58) Field of Classification Search
CPC ... A61B 5/1123; A61B 5/1124; A61B 5/1128; A61B 5/4585; A61B 5/726; A61B 5/7264; A61B 5/4519; A61B 5/4533; A61B 2505/09
See application file for complete search history.

(56) References Cited

U.S. PATENT DOCUMENTS

| | | |
|---|---|---|
| 8,187,209 B1 | 5/2012 | Giuffrida |
| 2011/0201904 A1 | 8/2011 | Cusimano Reaston |
| 2011/0270132 A1 | 11/2011 | Mezghani et al. |
| 2012/0130280 A1 | 5/2012 | Lee |
| 2015/0019135 A1* | 1/2015 | Kacyvenski ......... A61B 5/0488 702/19 |
| 2015/0257682 A1* | 9/2015 | Hansen ................ A61B 5/1128 382/103 |

* cited by examiner

REALTIME BIOFEEDBACK MECHANISM AND DATA PRESENTATION FOR KNEE INJURY REHABILITATION MONITORING AND A SOFT REAL TIME INTELLIGENT SYSTEM THEREOF

CROSS-REFERENCE TO RELATED APPLICATIONS

The present application claims priority to Brunei Patent Application No. BN/N/2014/0036, entitled "Realtime Biofeedback Mechanism and Data Presentation for Knee Injury Rehabilitation Monitoring and a soft real time intelligent system thereof" and filed on Apr. 3, 2014, the contents of which are hereby incorporated by reference.

FIELD OF THE INVENTION

The present invention relates generally to rehabilitation therapy systems and methods. Particularly, the present invention relates to providing a real-time decision supporting tool for physiatrists, physiotherapists, clinicians and subjects as well to evaluate and monitor the recovery progress of ACL reconstructed/injured subjects during different rehabilitation activities. More specifically, the present invention relates to devices and methods utilizing body mounted kinematics and neuromuscular sensors coupled to computers to record body movements for rehabilitation therapy and real time visual biofeedback analysis. The invention finds particular application in relation to determining a recovery progress and a status/class/level of recovery of a knee joint of a patient's limb from Anterior Cruciate Ligament injury and it will therefore be convenient to describe the invention in that environment. It should be understood however that the invention may be implemented in other environments.

BACKGROUND OF THE INVENTION

Rehabilitation following ACL injury or an ACL Reconstruction (ACLR) is an essential part of a full recovery and can span over several months. The rehabilitation process can be subdivided into various statuses/classes/levels, with each level having its own instructions, directions, rehabilitation guidelines and functional goals. During the rehabilitation process, the physiotherapist exercises their best professional judgment to determine the current state of recovery and devise appropriate treatment plan based on the same. As an individual's progress is variable, this treatment plan must be individualized for optimal return to activity and hence, accurate determination of the recovery progress and a status/class/level of recovery become crucial.

As such, systems utilizing visual Electromyographic (EMG) feedback are being used during rehabilitation processes. Patients have experienced improvement in muscle function following use of EMG feedback. However, currently marketed visual biofeedback systems provide minimal information to either the clinician or patient about the recovery progress and a status/class/level of recovery. The feedback that is most commonly provided by these systems is sensing strength of muscular effort and providing output corresponding to the sensed strength.

Evaluation of progress in a rehabilitation therapy program is problematic in part because of the small increments in the improvement of individuals. Current rehabilitation evaluation instruments and methods are not best adopted for the desired function. Often the rehabilitation evaluation instruments and methods are too crude and reliance has to be placed substantially upon what is observed by rehabilitation clinicians. Relying extensively upon observations of the rehabilitation clinicians makes the outcome prone to human errors. In any event, it has not been possible to determine a recovery progress and a status/class/level of recovery of a knee joint of a patient's limb from Anterior Cruciate Ligament injury in real time.

In view of this problem, there remains a need to provide a method and a system for real-time visualisation and determination of a recovery progress and a status/class/level of recovery of a knee joint of a patient's limb from ACL injury.

SUMMARY OF THE INVENTION

According to one aspect of the present invention there is provided a real time visualization and determination method for determining a recovery progress and a status/class/level of recovery of a knee joint of a patient's limb from Anterior Cruciate Ligament (ACL) injury, comprising the steps of receiving data pertaining to patient activity set, the data comprising (i) multiple super-imposed bio-signals from an electromyogram (EMG) for one or more muscles of one or both limbs of the patient, the muscles including vastusmedialis, vastuslateralis, semitendinosus, biceps femoris and gastrocnemius; and (ii) signals pertaining to three dimensional kinematics measurement as obtained from a motion sensor set; processing the signals from the EMG and the signals pertaining to three dimensional kinematics measurement to extract wavelet features; and evaluating the wavelet features thus extracted to determine an initial estimate of the extent of rehabilitation and a recovery classification of the patient's limb from ACL injury.

According to further aspect of the present invention there is provided a real time visualization and determination system for determining a recovery progress and status/class/level of recovery of a knee joint of a patient's limb from Anterior Cruciate Ligament (ACL) injury, comprising an input interface circuit, for receiving data pertaining to patient activity set, the data comprising (i) signal from an electromyogram (EMG) for one or more muscles of one or both limbs of the patient, the muscles including vastusmedialis, vastuslateralis, semitendinosus, biceps femoris and gastrocnemius; and (ii) signals pertaining to three dimensional kinematics measurement as obtained from a motion sensor set; a processing module forming part of a processor and being in operational interconnection with the input interface circuit, the processing module being configured to process the signals from the EMG and the signals pertaining to three dimensional kinematics measurement to extract wavelet features; a comparator module forming part of the processor for comparing the wavelet features thus extracted with data/signals stored in a database to determine an initial estimate of the extent of rehabilitation and a recovery classification of the patient's limb from ACL injury; and an output interface circuit being in operational interconnection with the processor for providing as an output the initial estimate of the extent of rehabilitation the patient's limb from ACL injury.

The visualization system is state-of-the-art in health care technology and provides real time quantitative feedback for physiatrists, physiotherapists, clinicians, sports trainers and orthopedic surgeons for monitoring the rehabilitation progress of ACL-R and/or injured subjects. The system can be used by sports medicine centers and performance monitoring and optimization centers for athletes and soldiers.

Further preferred features and advantages of the invention will be apparent to those skilled in the art from the following description of preferred embodiments of the invention, which should not be considered to be limiting of the scope of the invention as defined in the preceding statements, or in the claims appended hereto.

BRIEF DESCRIPTION OF THE DRAWINGS

Preferred embodiments of the present invention will now be described with reference to the accompanying drawings. These embodiments are given by way of illustration only and other embodiments of the invention are possible. Consequently, the particularity of the accompanying drawings is not to be understood as superseding the generality of the preceding description.

In the drawings.

Figure 1:
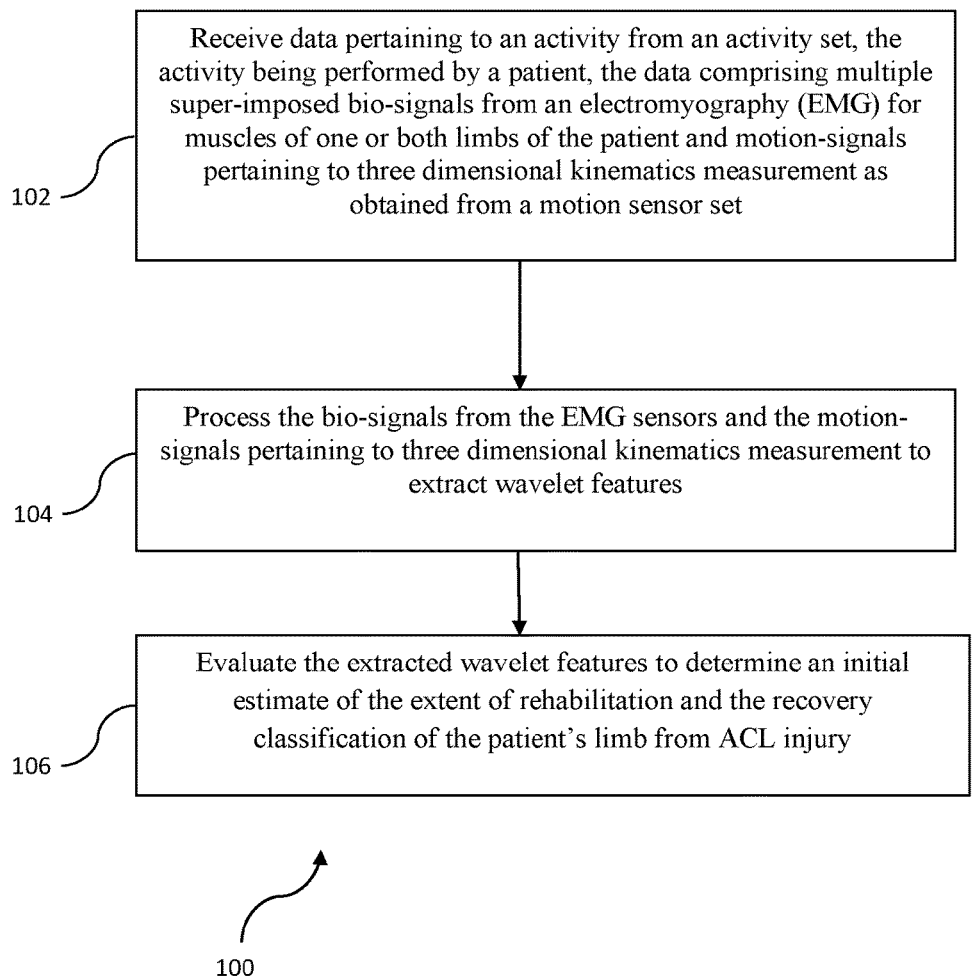
FIG. 1 shows a flow chart of the process in accordance with the teachings of the present invention.

Further, skilled artisan will appreciate that elements in the drawings are illustrated for simplicity and may not have been necessarily drawn to scale. For example, the flow charts illustrate the method in terms of the most prominent steps involved to help improve understanding of aspects of the invention. In terms of construction of device or system, one or more components may have been represented in the drawings using conventional symbols or using a simple block and the drawings may show only those specific details that are pertinent to understanding the embodiment of the present invention so as not to obscure the drawings with details that will be readily apparent to those or ordinary skill in the art having benefit of the description herein.

DETAILED DESCRIPTION

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated system and such further applications of the principles of the invention as illustrated and described herein being contemplated as would normally occur to one skilled in the art to which the invention relates. It will be understood by those skilled in the art that the foregoing general description and the following detailed description are exemplary and explanatory of the invention and not intended to be restrictive thereof.

Reference throughout this specification to "an aspect", "another aspect", or similar language means that a particular feature, structure of characteristics described in connection with the embodiment is included in at least one embodiment of the present invention. Thus, appearances of the phrase "in an embodiment", "in another embodiment" and similar language throughout this specification may, but not necessarily, all refer to the same embodiment.

The terms "comprise", "comprising", or any other variations thereof, are intended to cover a non-exclusive inclusion, such that a process or method that comprises a list of steps does not include only those steps but may include other steps not expressly listed or inherent to such process or method. Similarly, one or more devices or systems or sub-systems or elements or structures or components proceeded by "comprises . . . a" does not, without more constraints, preclude the existence of other or additional devices or systems or sub-systems or elements or structures or components.

Unless otherwise defined, all technical and scientific terms used herein have the same meaning as commonly understood by one of ordinary skill in the art to which this invention belongs.

Referring to FIG. 1, in accordance with one embodiment of the present invention the method (100) for determining extent of rehabilitation and recovery classification of a knee joint of a patient's limb from Anterior Cruciate Ligament (ACL) injury, using a real-time visualization system, comprises the steps of receiving (102) data pertaining to an activity from an activity set, the activity being performed by a patient, the data comprising (i) multiple super-imposed bio-signals from electromyography (EMG) sensors placed on one or more muscles of one or both limbs of the patient, the one or more muscles including vastusmedialis, vastuslateralis, semitendinosus, biceps femoris and gastrocnemius; and (ii) motion-signals pertaining to three dimensional kinematics measurement obtained from a motion sensor set; processing (104) the bio-signals from the EMG and the motion-signals pertaining to three dimensional kinematics measurement to extract wavelet features; and evaluating (106) the extracted wavelet features to determine an initial estimate of the extent of rehabilitation and the recovery classification of the patient's limb from ACL injury.

In an embodiment of the present invention, the motion-signal pertaining to kinematics measurement comprises signals pertaining to three dimensional angular rates and three dimensional linear acceleration obtained during the activity. Further, the kinematics measurement comprises three dimensional joint orientation measurements. Furthermore, the three dimensional joint orientation measurements include one or more of: joint flexion or joint extension; joint abduction or joint adduction; joint rotation; and actuation timings of different muscles for the activity.

In a particular embodiment, the input data can be various types and can include:

- 3-D angular rates and 3-D linear acceleration using wireless motion sensors placed on shanks and thighs on both legs, and trunk;
- Raw EMG signals from vastusmedialis, vastuslateralis, semitendinosus, biceps femoris and gastrocnemius muscles from both legs;
- Video recording for each activity monitored from front and side of ACL-R leg; and
- Linear acceleration signals from ankle of each leg for the determination of relevant gait cycle in real time measurements.

Figure 2:
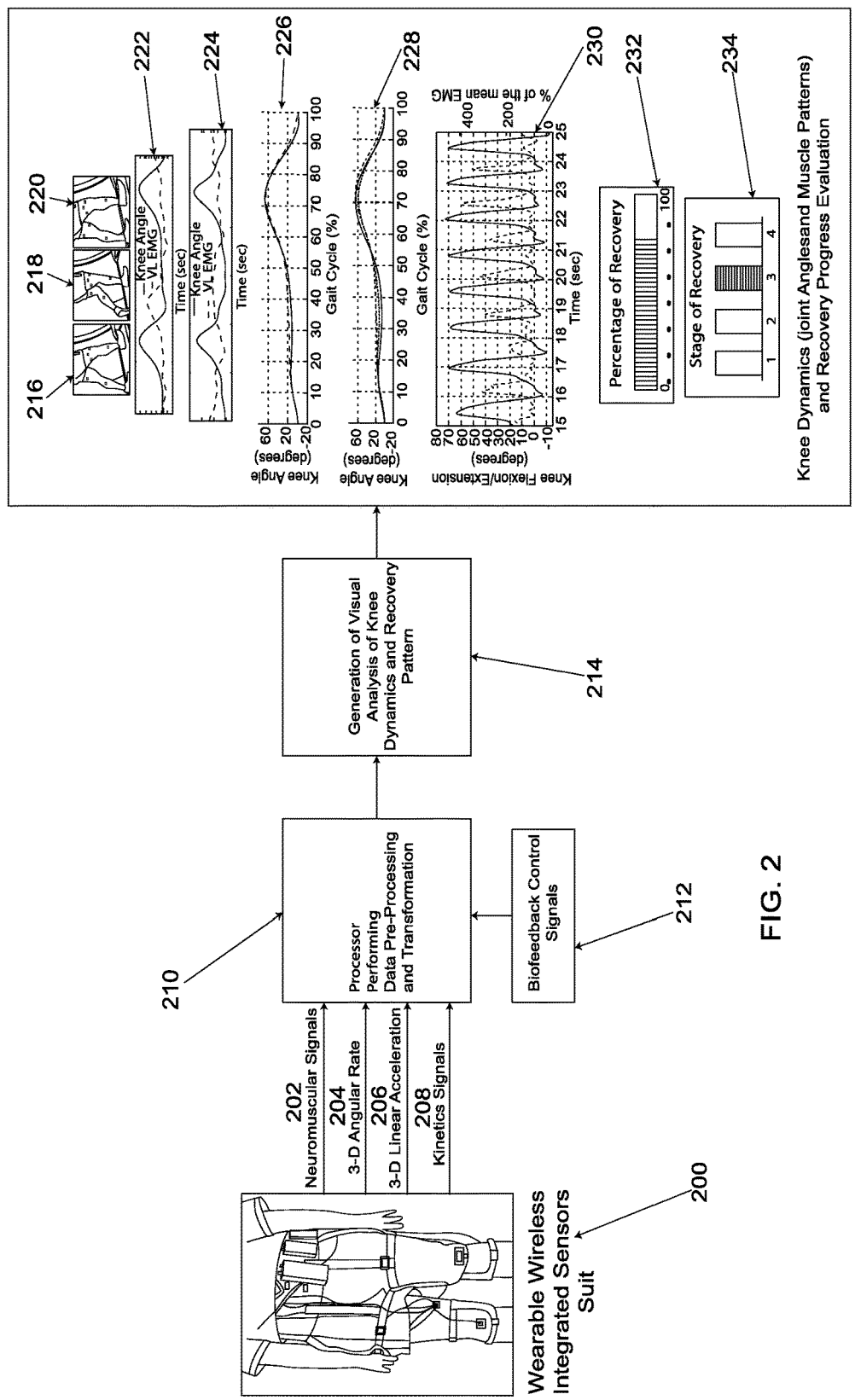
FIG. 2 shows a combined scheme in accordance with an embodiment of the present invention.

For $i^{th}$ human test subject ($S_i$), a complete raw input data set (I) for one rehabilitation activity can be presented as in equation 1:

$$I_{S_i} = \{K_1, K_2, \ldots, K_m\} \cup \{E_1, E_2, \ldots, E_n\} \cup \{V_1, V_2, \ldots, V_r\} \quad \text{Eq. 1}$$

Where $K_m$ represents the $m^{th}$ kinematics input feature recorded using a motion sensor, $E_n$ represents the $n^{th}$ EMG input data recorded using electromyography unit and $V_r$ represents $r^{th}$ frame of a video recording of an experiment (trial of an activity). These input signals are used to generate recovery status and/or visual biofeedback for each subject after processing using custom-developed knee injury rehabilitation visualization system as illustrated in FIG. 2. The kinematic input features are extracted from body-mounted motion sensors that are used to measure the subject's lower extremity motion during walking and balance testing, in terms of angular rate and linear acceleration. The 3-D angular rates and 3-D linear accelerations are the kinematics parameters for the input data set (I) for each subject which is used by the embedded system developed to determine the 3-D knee joint rotational movements. In general, a set 'K' of m kinematics parameters ($K_1, K_2, \ldots, K_m$) provided by s sensors can be presented as in equation 2:

$$K = \{a_{x_1}, a_{y_1}, a_{z_1} \ldots, a_{x_s}, a_{y_s}, a_{z_s}\} \cup \{\omega_{x_1}, \omega_{y_1}, \omega_{z_1}, \ldots, \omega_{x_s}, \omega_{y_s}, \omega_{z_s}\} \quad \text{Eq. 2}$$

Where $a_x$, $a_y$ and $a_z$ are linear accelerations in x, y and z axes, respectively and $\omega_x$, $\omega_y$ and $\omega_z$ are angular rates around x, y and z axes, respectively.

In some instances, superimposed bio-signals may be received as direct input or may receive data other than superimposed bio-signals as input and want to receive the superimposed bio-signals as an output, in which case, the method can generate a variety of superimposed bio-signals and some are:

knee flexion/extension with each of the processed EMG signals (envelopes) from different muscles for each rehabilitation activity monitored;

knee abduction/adduction with each of the processed EMG signals (envelopes) from different muscles for each rehabilitation activity monitored; or Knee rotation with each of the processed EMG signals (envelopes) from different muscles for each rehabilitation activity monitored.

Therefore, the electric potential generated by skeletal muscles provide the raw EMG signals (in mV) for the input data set (I) for each subject which are used by the knee injury rehabilitation visualization system developed as illustrated in FIG. 2 in order to extract useful features and determine the neuromuscular activity of healthy/ACL-R subjects. In general, the EMG signals (E) recorded at a given sampling rate from n channels (i.e. n muscles) a subject for an activity can be presented as in equation 3:

$$E = \{E_1, E_2 \ldots, E_n\} \quad \text{Eq. 3}$$

By way of a non-limiting example, as illustrated in FIG. 2, the patient may be provided with wearable wireless integrated sensor suit (200) which can provide neuromuscular signals (202), signals pertaining to 3-D angular rate (204), signals pertaining to 3-D linear acceleration (206) and kinetics signals (208). These signals are received by the processor (210), which performs data pre-processing and transformations. The processor (210) is able to additionally receive biofeedback control signal (212) with which the processor (210) compares the processed and transformed signals and generates visual analysis of knee dynamics and recovery pattern (214) A sample output is represented on the extreme right hand side of FIG. 2, wherein the output includes, one or more pictures or videos of the patient undergoing the exercise (216, 218, 220). The sample output also includes one or more graphs that represent real time signals as derived from the patient (222, 224) and one or more bio-feedback control signals (226 and 228). The bio-feedback control signals (226 and 228) refers to pattern set during pre-injury, injury, post-injury (surgery) and post-surgery period as well as the normal pattern to compare the real-time signals. The bio-feedback control signals can be signals of the healthy person to compare with the real-time signals of the injured person so as to calculate the progression or recovery data. It is also feasible to represent the bio-feedback control signal and the real-time signal in single graph as shown by the fifth graph taken from the top (230). The sample output also includes percentage recovery (232) which is shown on a scale of 100 (any other scale can however be adopted). The sample output furthermore includes an indication regarding a stage of recovery (234). While in FIG. 2, the stage of recovery is illustrated to be shown on a scale of 4, any other suitable scale can be adopted.

Preferably, the bio-signals are full wave rectified and low pass filtered to generate envelope data comprising wavelet features. More particularly, for the purposes of generating EMG envelope data and superimposed bio-signals, the raw EMG data for different muscles can be full wave rectified and low pass filtered to generate linear envelopes. The linear envelopes can provide useful information for assessing the strength/activation of different muscles for inter- and intra-subjects comparison. Before comparing the EMG amplitude, the data were normalized for each subject using mean value of the signal of each stride for respective muscles and data were represented as percentage of mean. These EMG envelopes, 3-D knee orientations and other relevant signals are then superimposed to show in a single graph. The superimposed bio-signals along with videos recorded during different exercises for can be provided for visual biofeedback purposes. The visual biofeedback provides for monitoring of bio-signals based on the processed motion and EMG data, and videos recorded during different experiments. The visual biofeedback not only provides visualization of the variations and activation patterns of kinematics and EMG signals but it also presents the superimposition/overlapping of both signals. Thus, the physiatrists and physiotherapists can confirm or disconfirm the contraction of different muscles of a subject with respect to his/her knee orientation movements. This biofeedback can be assessed by physiatrists, physiotherapists and clinicians and they can modify the individual's rehabilitation protocol and store these pattern set for updating the recovery state of a subject and for later performance comparison. The visual analysis was further enhanced by recording and displaying the video of affected lower limb for each subject during each activity. The recorded video of lower limbs' movements can also be shown (at slow speed with different options if required e.g. frame by frame, forward/backward) with corresponding knee orientations and EMG patterns to physiotherapists/physiatrists in order to observe any alterations in the knee dynamics for ACL-R subjects. Hence, corrective measures and muscle conditioning can be applied by physiotherapists/physiatrists in order to improve the recovery status of the knee and monitoring of objective rehabilitation progress can be used as a motivation tool for ACL-R subjects.

The method further comprises obtaining, by the real time visualization system, linear acceleration signals and calculating gait cycles from the linear acceleration signals.

In a preferred aspect, the step of evaluating comprises comparing the extracted wavelet features with data or signals stored in a database, wherein the data or signal stored in the database corresponds to data or signal obtained from the activity being performed by one or more healthy subjects; data or signal for the activity obtained for a rehabilitating joint of at least one other patient; data or signal for the activity obtained for an intact joint of at least one other patient; data or signal for the activity as obtained for a rehabilitating joint of the same patient taken in the past; data or signal for the activity as obtained for an intact joint of the same patient taken in the past; and data or signal for the activity obtained for an intact joint of the same patient taken during the current activity.

In yet another preferred aspect, the step of comparing comprises a step of generating a superimposed bio signal, if the extracted wavelet features are compared with one or more of: data or signal for the activity obtained for a rehabilitating joint of the same patient, taken in the past; data or signal for the activity obtained for an intact joint of the same patient taken in the past; and data or signal for the activity obtained for an intact joint of the same patient taken during the current activity.

In a preferred aspect, activation timings, duration and normalized strength of different muscles monitored for each rehabilitation activity within same and/or different legs of an ACL-R subject may be compared with the average of these parameters of a group of healthy subjects.

In yet another preferred aspect, 3-D knee movements (flexion/extension, abduction/adduction and rotation) of ACL-R leg of the subject may be compared with anterior cruciate ligament intact (ACL-I) of the same subject for each rehabilitation activity.

In still another preferred aspect, 3-D knee movements (flexion/extension, abduction/adduction and rotation) of ACL-R leg of a subject may be compared with average 3-D movements of healthy subjects for each rehabilitation activity.

In still another preferred aspect, the step of comparing comprises comparing the extracted wavelet features with clusters of data or signals stored in a database, the clusters having been formed using a fuzzy clustering method and the comparison with the clusters of data or signals providing an initial estimate of the extent of rehabilitation and a recovery classification of the patient's limb from ACL injury.

By way of a non-limiting example, the recovery progress of an ACL-R subject for each rehabilitation activity monitored as compared to a group of healthy subject may be expressed on percentage basis. Alternatively, the recovery class (level/stage) of an ACL-R subject for each rehabilitation activity can be provided as output in a graphical form. Alternatively, an overall recovery class (level/stage) of an ACL-R subject combined for all rehabilitation activities can be monitored and shown in a graphical form. The steps adopted by the method in doing so will be described in detail in the following paragraphs. However, it may be noted that apart from the above, the user can interact with a system software tool implementing the method to tailor make the manners of providing the output as per his/her convenience. Also, the user can implement different methods as system software tools for calculating the rehabilitation extent or can modify the proposed methods to suit needs.

Figure 3:
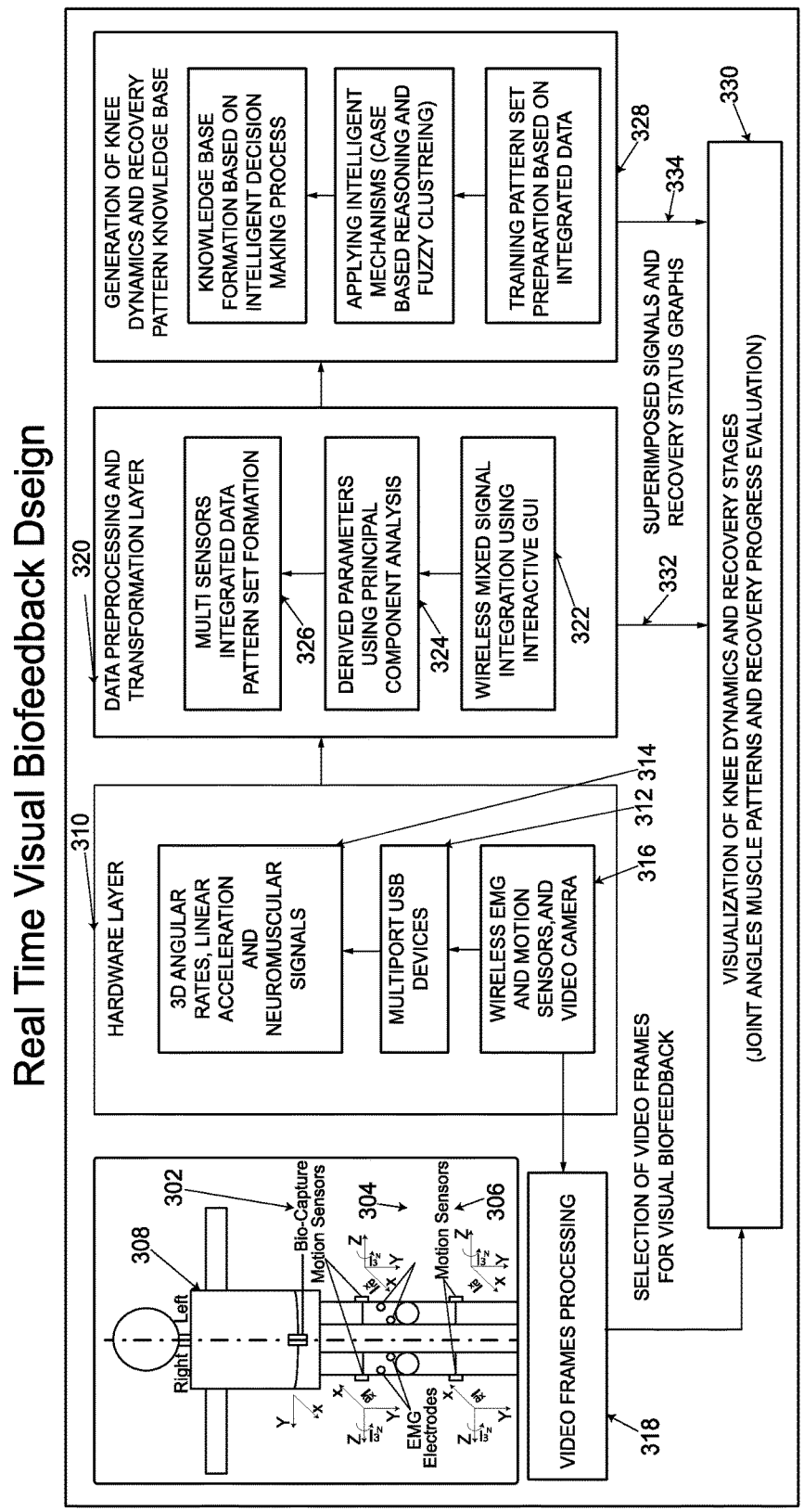
FIG. 3 shows an elaborate scheme in accordance with another embodiment of the present invention.

Referring to FIG. 3, bio-capture motion sensors (302), EMG electrodes (304) and motion sensors (306) are located with respect to the patient (308) and signals i.e. EMG signals, motion sensor signals and video camera signals are received by hardware layer (310). These signals can be stored on a memory such as a USB device or/and Programmable System-on-Chip (PSoC) (312) for later use or can be used in real time basis. The hardware layer derives 3-D angular rates, linear acceleration rates and neuromuscular signals (314) from the EMG signals, and motion sensor signals (316). The signals from video camera (part of 316) are also processed by video frame processing (318) to enable selection of video frames which can be used for the purposes of visual biofeedback.

The 3-D angular rates, linear acceleration rates and neuromuscular signals (316) as derived by the hardware layer (310) are received by the data pre-processing and transformation layer and (320) signal mixing or integration occurs. During this process, the user can interact and control the mixing and integration via an Interactive graphical user interface (IGUI) (322). Once the signals have been mixed/integrated, principal component analysis is performed to derive parameters (324) and patterns are formed for the multi-sensor integrated data (326).

In an off-line manner the derived parameters and integrated data are used as training pattern set for training using fuzzy logic system. Once the fuzzy logic system has been partly trained, further training can be imparted by applying intelligent mechanisms such as case based reasoning and fuzzy clustering to yield a knowledge base (or a database integrated with set of rules for the pattern set stored) (328). The knowledge base formation is also based on intelligent decision making process.

To enable visualization of knee dynamics and recovery stages such as joint angle muscle patterns and recovery pattern evaluation, the patient specific superimposed signals (332) are compared with the superimposed signals as contained in the knowledgebase (334) and based on the outcome of the comparison; recovery stage and progress of recovery are provided to the user (330).

Recovery Progress Indicator:

By way of illustration, in order to assess the recovery progress of a particular individual after ACL reconstruction, a numerical value can be computed that correlates to deviation of an ACL-R subject's data from the normal/healthy ambulation and postural control data. By way of a non-limiting example, the percentage of recovery progress score ($R_p$) for each activity i (i=1 . . . 5) can be calculated as follows:

$$R_{P_i} = \left[\frac{1}{1 + \alpha \times dist(\vec{C}_{H_i}, \vec{C}_{R_i})}\right] \times 100 \quad (1)$$

where $\vec{C}_H$ and $\vec{C}_R$ are n-dimensional vectors, representing the cluster center for healthy subjects for an activity and the transformed vector of average values of parameters for an activity for a new ACL-R subject, respectively, and $\alpha$ is a positive constant. $R_p$ can provide an approximate percentage of recovery progress for an ACL-R subject. The dist was computed using the Mahalanobis distance (2) which is a better distance measure for pattern recognition problems [78].

$$dist(\vec{C}_{H_i}, \vec{C}_{R_i}) = \sqrt{(\vec{C}_{R_i} - \vec{C}_{H_i})^T S^{-1} (\vec{C}_{R_i} - \vec{C}_{H_i})} \quad (2)$$

Where S is the covariance matrix for cluster of healthy subjects. The Mahalanobis distance was preferred over Euclidean distance as it takes into account the covariance among the variables in calculating distances. Thus, the problems related to scale and correlations which are inherent with the Euclidean distance are avoided.

Determining the Current Stage of Recovery of a New Subject:

In case the subject is a new subject and the method can be still adopted to determine the current stage of recovery of such new subject. The identification of current recovery stage of a new subject can be done based on the given kinematics and EMG measurements provide useful complementary information in order to make adjustments in his/her rehabilitation process. The motion patterns, which are not easily observable, can be captured through instruments and used to design an automated system to distinguish the walking or postural control parameters of subjects. An automated identification system has been developed to assess a new subject's current recovery stage based on the patterns of 3-D kinematics and neuromuscular data during five different activities. For each activity, one classifier was trained and tested based on the groups (clusters) formed using fuzzy clustering technique. The classification model was developed by using adaptive neuro-fuzzy inference system (ANFIS). The ANFIS is a fuzzy Sugeno model that adapts the membership function parameters using neural network and learns from the given data set. The ANFIS based classification was preferred over simple distance metrics because it takes care of patterns and variations in kinematics signals and non-stationary nature of EMG data which may lead the recovery classification task challenging. ANFIS has been found more useful for building models for such inputs. It can effectively identify the stochastic changes in bio-signals, and can also deal with the impreciseness in measurements and variations due to subjects' physiological conditions as compared to only fuzzy rule based system or simple artificial neural network techniques. The ANFIS model was trained based on the 75% of data from groups generated during clustering and then tested on remaining 25% of data after transforming the input patterns.

Determining the Recovery Progress within the Identified Stage

After identifying the current stage of recovery of a new subject, a numerical value can also be computed to determine the similarity between the new subject and the average subjects of the identified group (i.e. centroid of the group). This information can be useful in distinguishing new subjects who belong to a group but their characteristics vary from ideal or average value of the subjects of the identified group. The percentage of recovery within a stage ($R_{stage}$) can be computed similar to (1) by changing the centroid $C_H$ with $C_{stage}$ representing the centroid of the current stage identified for the new subject (3).

$$R_{stage_i} = \left[\frac{1}{1 + \alpha \times dist(\vec{C}_{stage_i}, \vec{C}_{R_i})}\right] \times 100 \quad (3)$$

Overall Recovery Evaluation:

An overall assessment of the recovery stage of a subject can be done by combining results from individual evaluations for different activities. Due to variations in a subject's performance during a rehabilitation activity or incomplete information for training of the inference system (ANFIS), different stage of recovery may be identified in each activity for the same subject. A reliable decision fusion mechanism should be employed in order to achieve combined accurate results. In this study, the results of recovery stage evaluation from five ANFIS s have been combined using Choquet integral method. The Choquet integral is a non-linear functional defined with respect to a fuzzy measure g and its densities. The steps for computing the fusion of evaluations are described below.

Step 1: Let there be i=1 . . . 5 fuzzy inference systems (ANFIS), denoted by $y_1, y_2, \ldots y_5$.

Step 2: Calculate the accuracy of each of the ANFIS by using cross validation technique for each stage of recovery $stage_1, stage_2, \ldots, stage_4$ for each activity.

Step 3: Calculate fuzzy measure $g_i$ (degree of importance) of each ANFIS based on its performance calculated in step 2 using (4).

$$\begin{cases} g^i = \beta p_i, & i = 3 \\ g^i = (1-\beta)p_i, & i = 1, 2, 4, 5 \end{cases} \quad (4)$$

Where $p_i$ is the identification accuracy rate in the [0,1] interval, $\beta$ in interval [0,1] is a scaling factor for ANFIS s. The selection of i=3 in (4) is based on the reliability/high accuracy value of the third ANFIS (which is for walking activity at speed 8 km/h).

Step 4: Compute the $g_\lambda$ fuzzy measure by solving (5) such that $\lambda \in (-1, +\infty)$ and $\lambda \neq 0$.

$$\lambda + 1 = \prod_{i=1}^{5}(1 + \lambda g^i) \quad (5)$$

Step 5: Let for k=1 . . . 4 stages of recovery, $h_k(y_i)$ represent the partial evaluation of a subject A for stage k i.e. $h_k(y_i)$ indicates the certainty of the identification of subject A to be in stage k using the ANFIS $y_i$. Arrange $h_k(y_i)$ for each stage k=1 . . . 4 such that $h(y_0)=0$ and $h(y_1) \leq h(y_2) \leq \ldots \leq h(y_n)$ and then re-arrange corresponding g's for each stage. The values of $h(y_i)$s were calculated using the sub-membership generation method.

Step 6: Compute $g^i(A)$, a fuzzy measure for A, using (6) for each stage.

$$\begin{cases} g(A_1) = g^1 \\ g(A_i) = g^i + g(A_{i-1}) + \lambda g^i g(A_{i-1}), & 1 < i \leq 5 \end{cases} \quad (6)$$

Step 7: Compute the Choquet integral using (7) for each stage k=1 . . . 4.

$$e_k = \sum_{i=1}^{5}(h_k(y_i) - h_k(y_{i-1})) \cdot g(A_i) \quad (7)$$

Step 8: Select the stage of recovery with the highest value of e computed using (7) as the output (overall recovery stage) of the fuzzy integration.

In yet another preferred aspect, the step of comparing implements an adaptive neuro-fuzzy interface system for comparing the extracted wavelet features with clusters of data or signals stored in a database, to arrive at the initial estimate of the extent of rehabilitation and the recovery classification of the patient's limb from ACL injury.

In another preferred aspect, the method further comprises obtaining, by the real time visualization system, video signals from a video camera set, including front view video signals and side view video signals of the joint of the patient's limb.

In yet another preferred aspect, the method further comprises depicting, by the real time visualization system, the initial estimate of the extent of rehabilitation of the joint of the patient's limb from ACL injury along with the video signals to enable acceptance or modification of the initial estimate.

In still another preferred aspect, the method further comprises depicting, by the real time visualization system, the initial estimate of the recovery classification of the knee joint of the patient's limb from ACL injury along with the superimposed bio signal to enable acceptance or modification of the initial estimate.

In another preferred aspect, the method of visualization and determination further comprises repeating the steps for a plurality of patient activities.

Although, not necessarily within the purview of the claims and merely for the purposes of enabling a person to understand, it may be noted that processing steps for the developed hardware/software co-design architecture are divided into main phases:

Processing during the creation/formation of knowledge base for pattern set preparation using input data during the learning process. This is an offline process and is described in detail in the following paragraphs for illustrative purposes; and Real time data processing which produces visualization of bio-signals and recovery status (class and percentage of recovery). For evaluating the recovery status, the current, actual and testing pattern set will undergo matching for patterns from the knowledge base in order to produce recovery class and percentage of recovery, and to retain the existing pattern set or update the pattern set or store the current, actual and testing pattern as new pattern set for the formed knowledge base. During this phase, randomly chosen input pattern set produces the output using the black box/knowledge base (hidden to end user such as surgeon, trainer, patient, etc) created during the first phase above. This has been described in detail in the foregoing paragraphs.

Processes for Creation/Formation of Knowledge Base

The process for creation/formation of knowledge base (or a data pool with which comparison is done during the working phase) comprises the following steps:

(a) Data Acquisition: After setting up the sensors, the input signals are recorded simultaneously from all sensors (motion and EMG). In system designing step, upon completion of each session, the input data are exported to data store for further processing. Moreover, the video recordings are also done for all testing sessions in order to store the lower limb movements during each rehabilitation activity. In real time testing environment, the signals are acquired and processed at runtime.

(b) Data Processing for Motion and EMG Sensors: The 3-D knee joint orientation measurements (flexion/extension, abduction/adduction and internal/external rotation) are obtained after filtering 3-D angular rates/linear accelerations from four motion sensor units placed on the thigh and shank segments of both legs by performing computation. The data from motion sensor placed on trunk are also filtered and stored. The raw EMG signals for selected lower extremity muscles are filtered for removing the noise/motion artifacts.

(c) Data Integration and Synchronization: The integration of kinematics and neuromuscular data required the synchronization of both bio-signals as these signals were different in nature and recorded by using two devices. The signals are time-synchronized based on each rehabilitation activity. Data segmentation of kinematics and EMG signals was performed prior to feature extraction step and then different features were computed for each segment. The length of the segment depends on the rehabilitation activity monitored (e.g. for ambulatory activities, each gait cycle is a segment, for balance testing activities, time based segmentation is performed like 15 sec or 20 sec).

(d) Feature Set Computation: For each activity kinematics (knee flexion/extension, internal/external rotations and abduction/adduction, and 3-D trunk movements in sagittal, frontal and transversal planes) and EMG features (statistical features including maximum, minimum, mean absolute value (MAV), standard deviation and average power of the DWT coefficients) are computed. Using principal component analysis (PCA) these features are reduced and a PCA coefficient matrix is stored.

(e) Formation of Groups (Clusters) of Subjects: The intention of clustering was to separate the individuals into homogeneous groups based on the selected input kinematics and EMG features and their performance during different activities. Data from different subjects (ACL-R and healthy with no knee injury reported) were clustered and labeled using a semi-automatic process. The assignment of data points to each cluster was based on their similarity to each other rather than time since ACL reconstruction. This was essential because the sample space consisted of ACL-R subjects at different stages of recovery and time since injury may not directly correlate with amount of recovery for all subjects due to multiple factors (compliance to the rehabilitation protocol, type of surgery, age, gender etc.). The fuzzy clustering technique was used for partitioning the sample space (3-D kinematics and neuromuscular patterns for each activity for all subjects) and organizing the data into approximate clusters. The fuzzy clustering has been adopted as opposed to the crisp/classical clustering algorithms due to the imprecise nature of motion and neuromuscular parameters. This is generally difficult in domains like recovery classification or gait analysis where variations in data are more common and one object may belong to different groups with different degree of memberships. Fuzzy clustering provides an effective mechanism to deal with such uncertainties and intra- and inter-subjects' variations. Once the clusters were generated, the groups were manually verified and labeled with the assistance of physiotherapists and head of physical strength and conditioning as follows; the group of healthy subjects was identified and the label for each group was assigned based on the distance of its centroid from the centroid of healthy subjects' group ($C_H$). The centroid of each cluster (mean of the data points weighted by their degree of belonging to the cluster) represents the average behavior of the subjects belonging to that group. If the centroid of a cluster i ($C_i$) lie much closer to the centroid of healthy subjects' group, it implies that the ACL-R subjects (data points) belonging to ith group are at an advanced level of recovery stage. In contrast, a cluster j with centroid $C_j$ much far from $C_H$ represents the group of ACL-R subjects (data points) who are partially recovered or at an early stage of recovery. Thus, depending on the number of clusters determined, the group labels can be assigned based on the stage/phase of recovery from stage 1 (farthest to the group of healthy subjects) to stage n−1 (closest to the group of healthy subjects) with stage n representing the group of healthy subjects and n is the total number of clusters identified from the given data.

Hence, a knowledge base is created in order to manage the information about the subjects' profiles and their health/rehabilitation conditions. It contains different types of information including raw and processed data, domain knowledge, historical data available for subjects (pre-injury, post-injury), session data during convalescence, case library (problem-solution pair for rehabilitation monitoring), reasoning and learning models (trained intelligent methods) and other relevant data (e.g. subjects' profiles, gender, type of sports etc.). In general, the information in knowledge base (KB) can be represented as in equation 4:

$$KB=\{pre\_inj\_I_S^i, post\_inj\_I_S^j, post\_op\_I_S^k, T(pre\_inj\_I_S^i), T(post\_inj\_I_S^j), T(post\_op\_I_S^k), S_p, D, C, M_t\} \quad \text{Eq. 4}$$

where pre_inj_$I_S^i$: raw input data set (kinematics, EMG and video) of a group of subjects 'S' for different sports activities at pre-injury (i.e. healthy) stage for i sessions (i≥1)

post_inj_$I_S^j$: raw input data set (kinematics, EMG and video) of a group of subjects 'S' for different sports activities after ACL injury (i.e. before surgery) for j sessions (j≥1)

post_op_$I_S^k$: raw input data set (kinematics, EMG and video) of a group of subjects 'S' for different sports activities after ACL reconstruction (i.e. rehabilitation after surgery) for k sessions (k≥1)

T(pre_inj_$I_S^i$): processed input data set (kinematics, EMG and video) of a group of subjects 'S' for different sports activities at pre-injury (i.e. healthy) stage for i sessions (i≥1)

T(post_inj_$I_S^j$): processed input data set (kinematics, EMG and video) of a group of subjects 'S' for different sports activities after ACL injury (i.e. before surgery) for j sessions (j≥1)

T(post_op_$I_S^k$): processed input data set (kinematics, EMG and video) of a group of subjects 'S' for different sports activities after ACL reconstruction (i.e. rehabilitation after surgery) for k sessions (k≥1)

$S_p$: profile (e.g. gender, age, weight, height, type of injuries, sports activities etc) of p subjects D: domain knowledge (e.g. type of protocols followed for ACL-R subjects, local/standard norms for different ACL rehabilitation activities etc.)

C: case library consisting of problem-solution pairs (processed input, rehabilitation procedure followed, outcomes and possible suggestions) related to individuals or different group of subjects $M_t$: trained intelligent models for each activity t to be monitored Utilization of Data Transformation Formatted (Groups) Clusters and Application of Data Transformation Techniques:

During the real-time processing phase the method applies apply data transformations and uses the formed clusters in an intelligent manner. Particularly, PCA coefficient matrix from knowledge base (as stored during the future set computation stage) is applied to the kinematics and EMG data of current test subject in real time and the result is used for evaluating the recovery status and progress thereby, intelligently utilizing data transformations.

The recovery progress and the status/class/level of recovery for each subject are generated at real time by using the formed clusters and trained intelligent methods and metrics which are stored in the knowledge base. Thus the output is generated as recovery status/class/level and the progress of recovery of an ACL-R subject as compared to the group of healthy subjects using equation (1) and within the identified class using equation (3).

Figure 4:
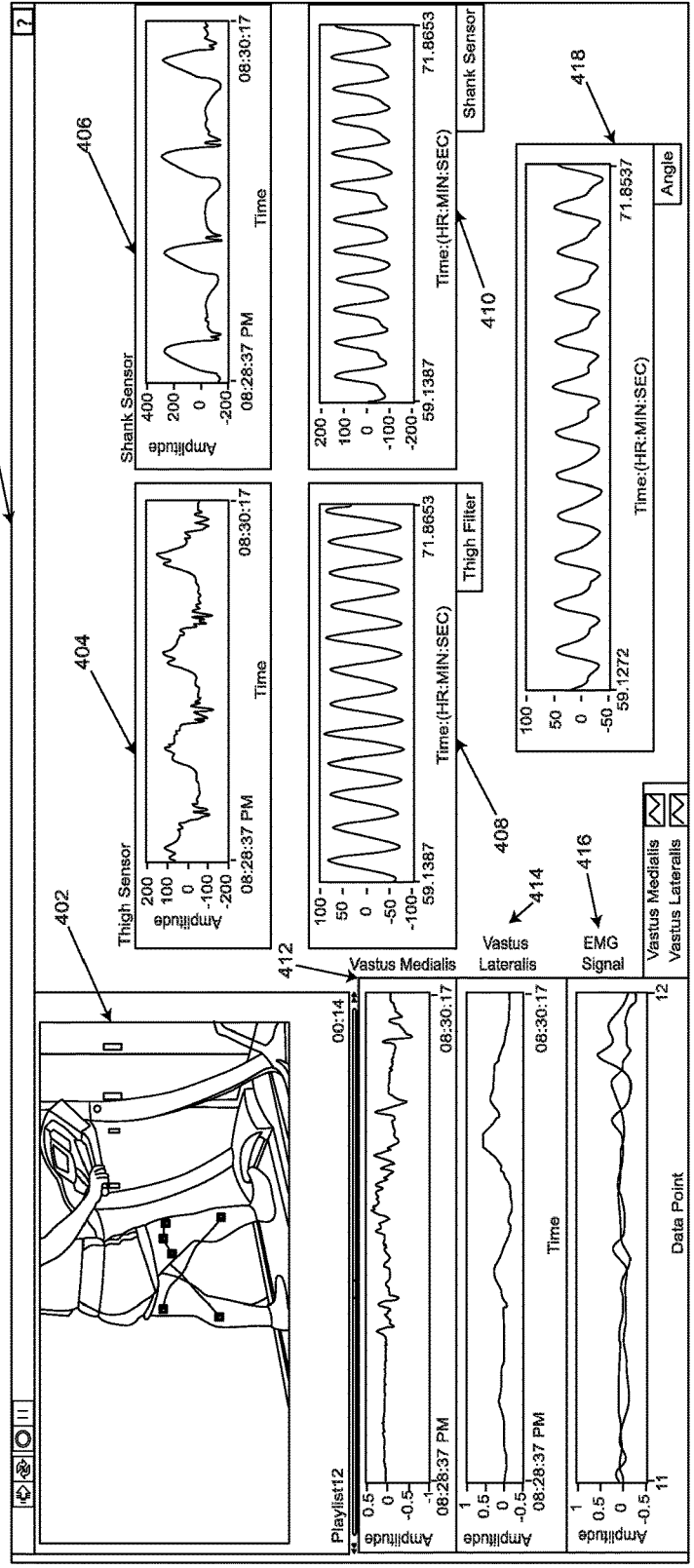
FIG. 4 illustrates a combined view as may be presented by the visualization system comprising various elements such as video of the subject performing the exercise, one or more individual EMG signals (in raw and/or in filtered form), one or more superimposed bio-signals, a percentage recovery data and a recovery stage data.

It may be preferred that the physiatrists, physiotherapists or the clinicians may be interested in viewing a combined snapshot and in which case, the output can include within a single window one or more the signals as captured, one or more of signals post processing and one or more conclusions. Referring to FIG. 4, it can be seen that a single output window (400) can be configured to contain the video signals (402) thus captured of the subject during exercise, one or more raw signals (from EMG and/or other sensors) (404, 406), one or more processed signals (408, 410) (including one more superimposed bio-signals (412, 414, 416) and one or more initial estimations of the extent of rehabilitation and a recovery classification of the patient's limb from ACL injury (418).

Figure 5:
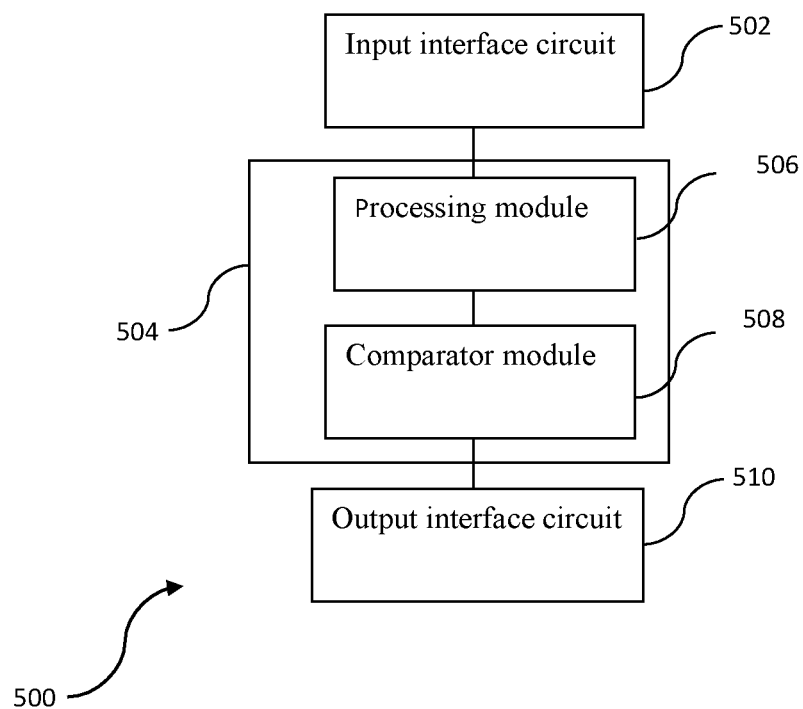
FIG. 5 illustrates a block diagram of the real time visualization system in accordance with an embodiment of the present invention.

Coming to the system perspective, as illustrated in FIG. 5, the real-time visualization system (500) comprises an input interface circuit (502), for receiving data pertaining to activity set, the activity being performed by patient, the data comprising (i) bio-signals from an electromyography (EMG) sensors placed on one or more muscles of one or both limbs of the patient, the one or more muscles including vastusmedialis, vastuslateralis, semitendinosus, biceps femoris and gastrocnemius; and (ii) motion-signals pertaining to three dimensional kinematics measurement as obtained from a motion sensor set; a processing module (506) forming part of a processor (504) and being in operational interconnection with the input interface circuit (502), the processing module (506) being configured to process the bio-signals from the EMG and the motion-signals to extract wavelet features; a comparator module (508) forming part of the processor (504) for comparing the extracted wavelet features with data or signals stored in a database to determine an initial estimate of the recovery progress and the class of recovery of the knee joint of the patient's limb from ACL injury; and an output interface circuit (510) being in operational interconnection with the processor (504) for providing as an output the initial estimate of the recovery progress and class of recovery of the knee joint of the patient's limb from ACL injury.

In a preferred aspect of the invention, the input interface circuit further receives video signals from a video camera set, including front view video signals and side view video signals and provides the same to the processing module of the processor.

In another preferred aspect of the invention, the output interface circuit depicts the initial estimate of the extent the recovery progress and the class of recovery of the knee joint of the patient's limb from ACL injury along with the video signals.

In a preferred aspect of the invention, the system can comprise of one or more sensor which provide the inputs signals. The sensors can for example, be motion sensor (MEMS) units, an EMG system and/or video camera. Each of the MEMS units, EMG system and the video camera can be adapted to transfer data there-from either using wireless technology or using a wired connection, with wireless data transfer being a preferred mode of data transfer.

While the real-time visualization system is said to be comprised of 4 elements or basic blocks, the 4 elements basic blocks can be further subdivided and/or the system can include additional elements/basic blocks. In this regard, the system can be comprised of many blocks nomenclature as per the function performed by each block. For example, the system can include:

(a) Module for data acquisition from wireless MEMS units;
(b) Module for data acquisition from wireless EMG system;
(c) Module for data acquisition from video camera;
(d) Motion data processing module;
(e) EMG data processing module;
(f) Visual pattern determination module;
(g) A knowledge base or a database storing the past data and/or data from any of (a) to (f);
(h) A data integration and synchronization module which assists in creation of superimposed bio-signals;
(i) Data transformation applying module;
(j) Envelope data and superimposed bio-signal generation module;
(k) Module for generation visual bio feedback;
(l) Module for performing the comparison using clusters other information as stored in the knowledge base;
(m) Module for determination of recovery progress and status/class/level of recovery; and
(n) Output module for providing output to the user.

Additionally, the system can include means for obtaining feedback from the physiatrists, physiotherapists or the clinicians. The feedback could be relating to acceptance of the results as output by the system or modifications to output or suggestions relating to modification or suggestions enabling the system to learn etc.

In a preferred aspect of the invention at least the processing and the comparator modules can be integrated together and form part of a single device, which for example can be a computer system. The computer system can include set of instructions that can be executed to cause the computer system to perform the method as a whole or in part. The computer system can operate as a standalone device or may be connected e.g., using a network to other computer systems or peripheral devices.

In a networked deployment, the computer system may operate in the capacity of a server or as a client user computer or as a peer computer system. The computer system can be implemented as or incorporated into various devices such as personal computer (PC), a tablet PC, a set-top box, a personal digital assistant (PDA), a mobile device, a palmtop computer, a laptop computer, a control system or any other machine capable of executing a set of instructions that specify actions to be taken by that machine.

Figure 6:
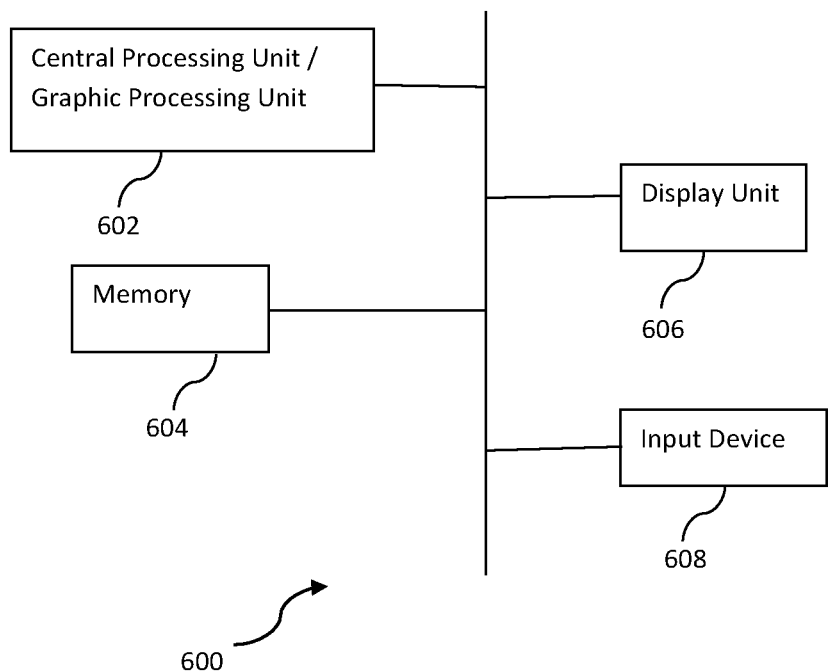
FIG. 6 illustrates a block diagram of another real time visualization system in accordance with yet another embodiment of the present invention.

As illustrated in FIG. 6, the computer system (600) may include a processor (602) e.g. a central processing unit (CPU), a graphic processing unit (GPU), or both. The processor may be one or more of general processors, digital signal processors, application specific integrated circuits, field programmable gate arrays, digital circuits, analog circuits, combinations thereof or other now known or later developed devices for performing the aforesaid action.

The computer system (600) may include memory (604). The memory can be main memory or a static memory or a dynamic memory. The computer system may further include display unit (606), such as Liquid crystal display, an organic light emitting diode, a flat panel display, as solid state display, a cathode ray tube, a projector, a printer or other devices for outputting determined information.

Additionally, the computer system (600) may include an input device (608) configured to allow a user to interact. The input device can be a number pad, a keyboard, a cursor control device such as a mouse or a joystick, touch screen display, remote control or any other device operative to interact with the computer system.

The invention provides for the following advantages:

The outputs provide a feedback as supporting information for clinicians, physiatrists, physiotherapists for observing the recovery progress of ACL-R subjects This information can be used for
  adjusting individual subject's rehabilitation protocol as per the requirements
  focusing on specific recovery problem areas
  performance comparison during rehabilitation stages for each monitored activity The intentions of designing this recovery assessment tool are to help in reducing duration and cost of recovery, and improving the rehabilitation process by providing accurate and timely information about the subjects' knee functionality.

As the present invention may be embodied in several forms without departing from the essential characteristics of the invention, it should be understood that the above described embodiment should not be considered to limit the present invention but rather should be construed broadly. Various modifications and equivalent arrangements are intended to be included within the spirit and scope of the invention.

What is claimed is:

1. A method implemented by a real time visualization system for determining extent of rehabilitation and recovery classification of a knee joint of a patient's limb from Anterior Cruciate Ligament (ACL) injury, the method comprising the steps of:

receiving data pertaining to an activity from an activity set, the activity being performed by a patient, the data comprising:
  multiple super-imposed bio-signals from electromyography (EMG) sensors placed on one or more muscles of one or both limbs of the patient, the one or more muscles including vastusmedialis, vastuslateralis, semitendinosus, biceps femoris and gastrocnemius; and
  motion-signals pertaining to three dimensional kinematics measurements obtained from a motion sensor set;
segmenting the bio-signals from the EMG sensors and the motion-signals pertaining to three dimensional kinematics measurement into a plurality of data segments, wherein a length of each data segment is based on the activity;
extracting wavelet features, after the segmentation, based on the plurality data segments; and
evaluating the extracted wavelet features to determine an initial estimate of the extent of rehabilitation and the recovery classification of the patient's limb from ACL injury.

2. The method of claim 1, wherein the motion-signal pertaining to the kinematics measurement comprises signals pertaining to three dimensional angular rates and three dimensional linear acceleration obtained during the activity.

3. The method of claim 1, wherein the three dimensional kinematics measurement comprises three dimensional joint orientation measurements.

4. The method of claim 3, wherein the three dimensional joint orientation measurements include one or more of:
  a. joint flexion or joint extension;
  b. joint abduction or joint adduction;

c. joint rotation; and d. actuation timings of different muscles for the activity.

5. The method of claim 1, wherein the bio-signals are full wave rectified and low pass filtered to generate envelope data comprising wavelet features.

6. The method of claim 1, further comprising obtaining, by the real time visualization system, linear acceleration signals and calculating gait cycles from the linear acceleration signals.

7. The method of claim 1, wherein the step of evaluating comprises comparing the extracted wavelet features with data or signals stored in a database, wherein the data or signal stored in the database corresponds to:

a. data or signal obtained from the activity being performed by one or more healthy subjects;

b. data or signal for the activity obtained for a rehabilitating joint of at least one other patient;

c. data or signal for the activity obtained for an intact joint of at least one other patient;

d. data or signal for the activity obtained for a rehabilitating joint of the same patient, taken in the past; and e. data or signal for the activity obtained for an intact joint of the same patient taken in the past.

8. The method of claim 7, wherein the step of comparing comprises a step of generating a superimposed bio signal, if the extracted wavelet features are compared with one or more of:

a. data or signal for the activity obtained for a rehabilitating joint of the same patient, taken in the past;

b. data or signal for the activity obtained for an intact joint of the same patient taken in the past; and c. data or signal for the activity obtained for an intact joint of the same patient taken during the current activity.

9. The method of claim 7, wherein the step of comparing comprises comparing the extracted wavelet features with clusters of data or signals stored in a database, the clusters having been formed using a fuzzy clustering method based on selected motion-signals, bio-signals, and information based on performance of patients during different activities, the comparison with the clusters of data or signals providing an initial estimate of the extent of rehabilitation and a recovery classification of the patient's limb from ACL injury.

10. The method of claim 9, wherein the step of comparing implements an adaptive neuro-fuzzy interface system for comparing the extracted wavelet features with clusters of data or signals stored in a database, to arrive at the initial estimate of the extent of rehabilitation and the recovery classification of the patient's limb from ACL injury, each cluster being semi-automatically assigned a label representing a stage of recovery.

11. The method of claim 1, further comprising obtaining, by the real time visualization system, video signals from a video camera set, including front view video signals and side view video signals of the joint of the patient's limb.

12. The method of claim 1, further comprising depicting, by the real time visualization system, a percentage of rehabilitation of the joint of the patient's limb from ACL injury along with the video signals, wherein the percentage is calculated based on a distance between a centroid of a cluster generated using data of a group of healthy subjects for the activity and a centroid of a cluster generated using the received data of the patient for the activity.

13. The method of claim 1, further comprising depicting, by the real time visualization system, the initial estimate of the recovery classification of the knee joint of the patient's limb from ACL injury along with the superimposed bio signal, wherein the real time visualization system receives one or more inputs from a user to enable modification of the initial estimate.

14. The method of claim 1, further comprises repeating the steps for a plurality of patient activities, wherein an overall assessment of the recovery classification is determined by combining results from evaluations of the plurality of patient activities.

15. A real time visualization system for determining a recovery progress and class of recovery of a knee joint of a patient's limb from Anterior Cruciate Ligament (ACL) injury, the system comprising:

an input interface circuit, for receiving data pertaining to activity set, the activity being performed by patient, the data comprising:

bio-signals from an electromyography(EMG) sensors placed on one or more muscles of one or both limbs of the patient, the one or more muscles including vastusmedialis, vastuslateralis, semitendinosus, biceps femoris and gastrocnemius; and motion-signals pertaining to three dimensional kinematics measurements as obtained from a motion sensor set;

a processor programmed and being in operational interconnection with the input interface circuit to:

process the bio-signals and the motion-signals to extract wavelet features, the processing includes receiving a control input from a user via an interactive graphical user interface for mixing signals derived based on the bio-signals and the motion-signals before extracting the wavelet features;

compare the extracted wavelet features with data or signals stored in a database to determine an initial estimate of the recovery progress and the class of recovery of the knee joint of the patient's limb from ACL injury; and an output interface circuit being in operational interconnection with the processor for providing as an output the initial estimate of the recovery progress and the class of recovery of the knee joint of the patient's limb from ACL injury.

16. The system of claim 15, wherein the input interface circuit further receives video signals from a video camera set, including front view video signals and side view video signals and provides the video signals to the processing module of the processor.

17. The system of claim 16, wherein the output interface circuit depicts, one or more bio-signals, one or more motion signals, one or more processed signals including one or more superimposed bio-signals, bio-feedback control signals referring to a pattern set during pre-injury, injury, post-injury, and post-surgery period to compare the one or more bio-signals, the initial estimate of the recovery progress and the class of recovery of the knee joint of the patient's limb from ACL injury along with the video signals in a single configurable output window.

18. The system of claim 15, wherein one or more feedbacks are received for modifying a tool from a plurality of tools implemented for determining the initial estimate.

19. The system of claim 15, wherein the recovery progress is determined after determining the class of recovery.

20. The system of claim 15, wherein one or more feedbacks are received for modification of the output.

* * * * *